(12) United States Patent
Funahashi

(10) Patent No.: US 6,976,231 B1
(45) Date of Patent: Dec. 13, 2005

(54) IMAGE SELECTING APPARATUS

(75) Inventor: Takeshi Funahashi, Kaisei-machi (JP)

(73) Assignee: Fuji Photo Co., Ltd., Kanagawa-ken (JP)

( * ) Notice: Subject to any disclaimer, the term of this patent is extended or adjusted under 35 U.S.C. 154(b) by 419 days.

(21) Appl. No.: 09/703,651

(22) Filed: Nov. 2, 2000

(30) Foreign Application Priority Data

Nov. 2, 1999 (JP) .................. 11/312144

(51) Int. Cl.$^7$ ............................................ G09G 5/00
(52) U.S. Cl. .................................................. 715/853
(58) Field of Search .............................. 345/764, 810, 345/853, 854; 382/131, 132; 715/764, 810, 715/841, 853, 854, 855

(56) References Cited

U.S. PATENT DOCUMENTS

| 4,258,264 A | | 3/1981 | Kotera et al. ................ 250/484 |
| 4,346,295 A | | 8/1982 | Tanaka et al. ............ 250/327.2 |
| 4,485,302 A | | 11/1984 | Tanaka et al. ............ 250/327.2 |
| 5,644,611 A | * | 7/1997 | McShane et al. ............. 378/98 |
| 5,740,267 A | * | 4/1998 | Echerer et al. ............. 382/132 |
| 5,954,650 A | * | 9/1999 | Saito et al. .................. 600/425 |
| 6,177,937 B1 | * | 1/2001 | Stockham et al. .......... 345/807 |
| 6,335,742 B1 | * | 1/2002 | Takemoto .................... 345/781 |
| 6,463,426 B1 | * | 10/2002 | Lipson et al. .................. 707/3 |

FOREIGN PATENT DOCUMENTS

| JP | 55-12429 | 1/1980 | ............ G01T 1/10 |
| JP | 56-11395 | 2/1981 | ............ G21K 4/00 |
| JP | 56-11397 | 2/1981 | ............ G21K 4/00 |

* cited by examiner

Primary Examiner—Kristine Kincaid
Assistant Examiner—Thanh Vu
(74) Attorney, Agent, or Firm—Sughrue Mion, PLLC

(57) ABSTRACT

An image selecting apparatus for selecting images of the same property is disclosed. The image selecting apparatus includes a storing device for storing a plurality of images, a display screen for displaying a list of the images stored in the storing device, image specifying device for specifying one of the images in the image list displayed on the screen, property item specifying component for specifying an image property item, and collective image selection component for collectively selecting all images having the same property as in the property item of the image specified by the property item specifying component and the image specifying device.

22 Claims, 3 Drawing Sheets

IMAGE SELECTING APPARATUS

BACKGROUND OF THE INVENTION

1. Field of the Invention

The present invention relates to an image selecting apparatus for collectively selecting one or more images having the same property.

2. Description of the Related Art

Radiation image recording and reproducing systems using stimulable phosphor storing a portion of energy of radiation (such as X rays, $\alpha$ rays, $\beta$ rays, $\gamma$ rays, electron rays, and ultraviolet rays) irradiated thereon and emitting light in accordance with the stored energy by being exposed to stimulating rays such as visible light have been known. In such a radiation image recording and reproducing system, information of a radiation image of a subject such as a human body is recorded on a stimulable phosphor sheet comprising a stimulable phosphor layer (the radiation image is photographed), and the stimulable phosphor sheet is scanned with the stimulating rays such as a laser beam to cause the sheet to emit the light. The light is then photoelectrically read to obtain an image signal (the radiation image is read), and the radiation image of the subject is output as a visible image on a recording medium such as a photosensitive material or on a display apparatus such as a CRT display, based on the image signal having been obtained (see Japanese Unexamined Patent Publication Nos. 55(1980)-12429, 56(1981)-11395, and 56(1981)-11397, for example).

In such a radiation image recording and reproducing system, images having been photographed are stored in storing means. In some cases, a radiologist or a doctor or the like selects a desired image while checking a list of the images stored in the storing means by using a display screen such as a CRT display in order to display or delete the selected image.

For example, all images of a patient or all images of a patient photographed in a certain medical examination are selected and displayed in some cases so that order of the images of the patient or order of the images of the patient in the medical examination can be confirmed. In other cases, whether or not density is uniform among all images is confirmed. Alternatively, all images of a patient or all images of a patient photographed during a particular medical examination may be selected and deleted.

In such a case, it is necessary for all images of a patient or all images photographed in a particular medical examination to be selected. However, in the case where all images having the same property, such as all the images of the patient or all the images photographed in the medical examination, are selected by using a conventional system described above, a radiologist or a doctor manually searches for and selects such images one by one while checking an image list displayed on a display screen.

When all the images having the same property are selected based on the image property such as the patient or the medical examination, it is time-consuming for the radiologist or the doctor to manually search for and select the images by checking the image list as has been conventionally carried out. Furthermore, all the images having the same property may not necessarily be selected and some images may slip through the selection.

SUMMARY OF THE INVENTION

The present invention has been conceived based on consideration of the above problems. An object of the present invention is therefore to provide an image selecting apparatus for enabling easy, prompt, and collective selection of images having the same property without omission.

In order to achieve the object described above, an image selecting apparatus of the present invention comprises:
storing means for storing a plurality of images;
a display screen for displaying a list of the images stored in the storing means;
image specifying means for specifying a desired one of the images from the image list displayed on the screen;
property item specifying means for specifying a desired one of image property items; and
collective image selection means for collectively selecting, in the case where the desired one of the images has been specified by the image specifying means and the desired one of the image property items has been specified by the property item specifying means, all images having the same property as in the specified property item of the specified image.

In the image selecting apparatus, the property items have a hierarchical structure. In the case where the image property item having been specified is in a hierarchical level other than a highest level, the collective image selection means can collectively selects all images having the same properties as in the image property items in the hierarchical level of the specified property item and in higher levels.

In the above apparatus, the collective image selection means can select the images from all the images stored in the storing means.

The above apparatus may further comprise output/display instruction means for inputting an output/display instruction for outputting or displaying the images having been collectively selected and output/display control means for outputting or displaying the images having been collectively selected, based on the output/display instruction.

The above apparatus may further comprise deletion instruction means for inputting a deletion instruction to delete, from the storing means, the images having been collectively selected, and deletion means for deleting the images from the storing means by receiving the deletion instruction.

According to the image selecting apparatus of the present invention, the apparatus comprises the image specifying means for specifying any one of the images from the image list displayed on the screen, the property item specifying means for specifying any one of the image property items, and the collective image selection means for collectively selecting the images having the same property as the property in the specified property item of the specified image. Therefore, by specifying the image and the property item by using the image specifying means and the property item specifying means, all images having the same property as in the specified property item of the image having been specified can be collectively selected. In this manner, the images having the same property can be selected easily, promptly and without omission.

DESCRIPTION OF THE PREFERRED EMBODIMENT

Hereinafter, an embodiment of the present invention will be explained in detail with reference to the accompanying drawings.

Figure 1:
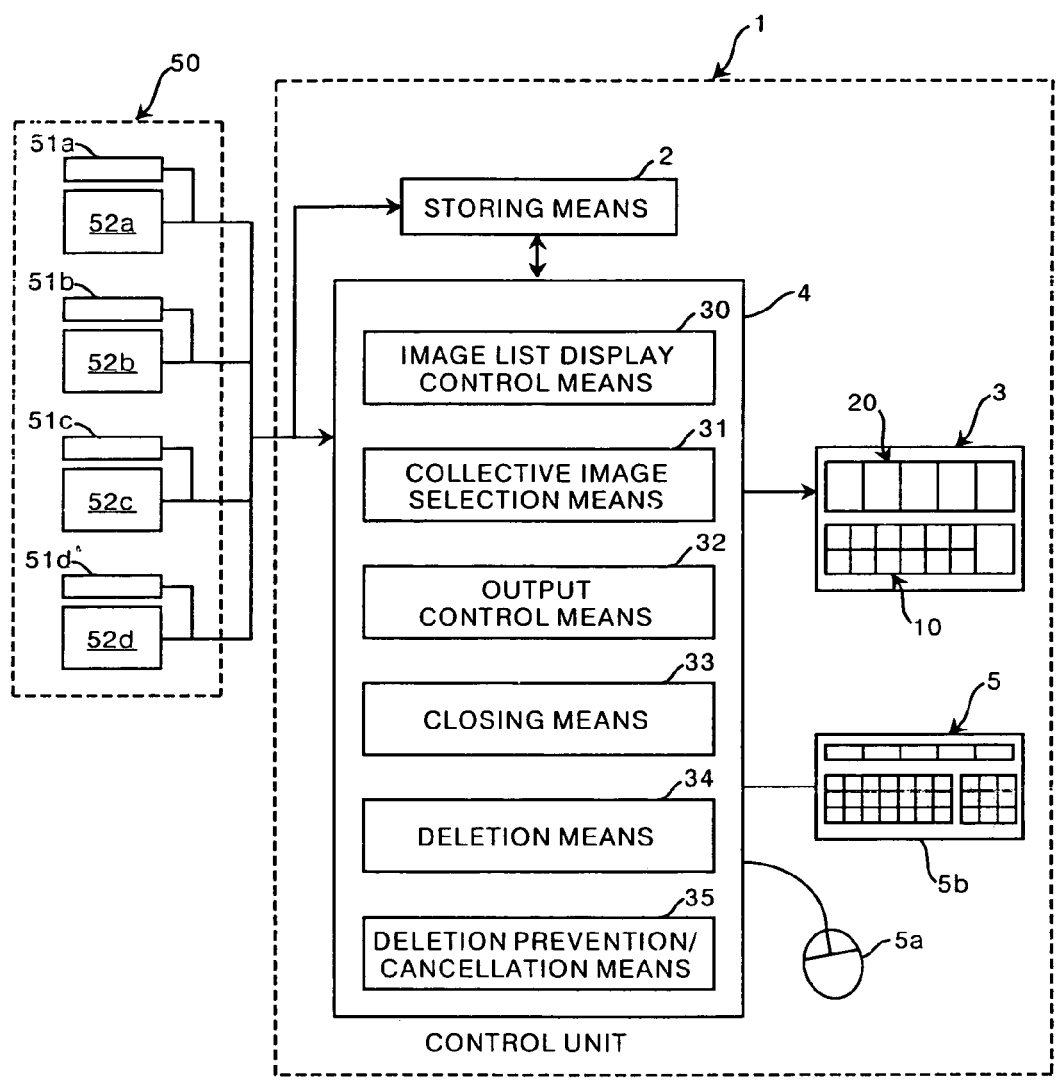
FIG. 1 is a block diagram showing an embodiment of an image selecting apparatus of the present invention.
Figure 2:
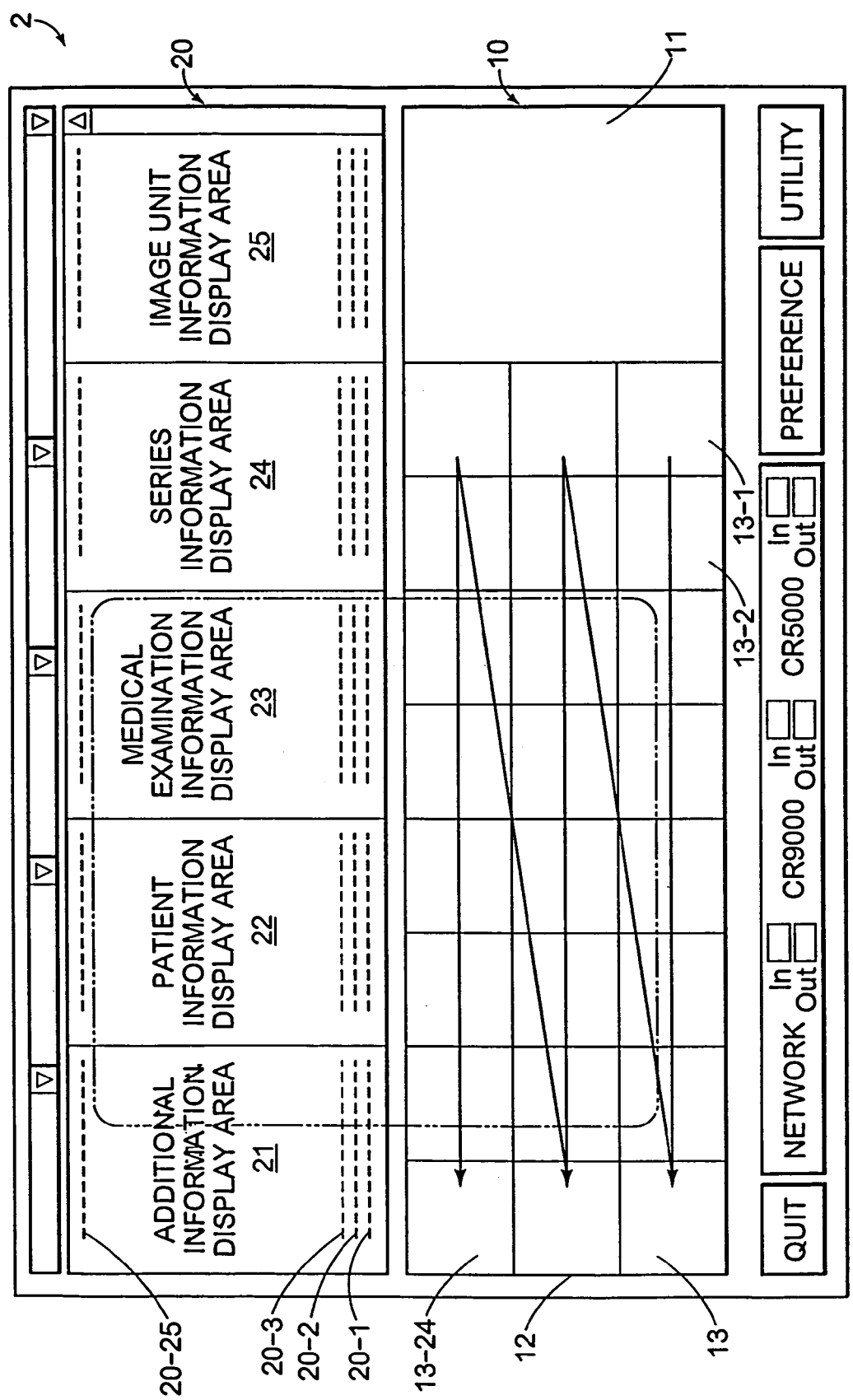
FIG. 2 shows an enlargement of a screen.

FIG. 1 is a block diagram showing an embodiment of an image selecting apparatus of the present invention, and FIG. 2 shows an enlargement of a screen shown in FIG. 1.

An image selecting apparatus 1 shown in FIG. 1 selects medical images photographed by using stimulable phosphor sheets. The image selecting apparatus 1 comprises storing means 2 for storing the images (image signals), a display screen 3 of display means such as a CRT display for displaying an image list or the like, a control unit 4 for carrying out various kinds of control and processing such as image selection, and an instruction input means 5 for inputting various kinds of instructions such as image specification, property item specification, and the like. The image selecting apparatus 1 is connected to an external system 50 which inputs the images (the image signals) and various kinds of accompanying information for the images.

The external system 50 comprises four reading apparatuses 51a~51d installed respectively in four photographing rooms each for obtaining the images (the image signals) by reading image information from the stimulable phosphor sheets on which radiation images have been recorded, and accompanying information input apparatuses 52a~52d respectively installed together with the reading apparatuses 51a~51d. The images read by the reading apparatuses 51a~51d are input to the control unit 4 while being linked with the accompanying information input from the accompanying information input apparatuses 52a–52d.

The screen 3 comprises an image display area 10 for displaying the images input from the external system 50 to the control unit 4 (the images based on the image signals input from the external system 50) and an accompanying information display area 20 for displaying the accompanying information input from the external system 50. An image list used in the present invention is displayed in the accompanying information display area 20. In other words, in this embodiment, the accompanying information of the images is displayed in the form of a list in the accompanying information display area 20 which will be explained later, and the list is used as the image list in the present invention.

As shown in FIG. 2, the image display area 10 comprises monitor display area 11 for body motion confirmation and a thumbnail image display area 12 for history confirmation. The thumbnail image display area 12 comprises 24 thumbnail image display frames 13 laid out in a grid pattern.

The accompanying information display area 20 comprises 5 display areas arranged in a row, that is, an additional information display area 21, a patient information display area 22, a medical examination information display area 23, a series information display area 24, and an image unit information display area 25, as shown in FIG. 2.

The accompanying information refers to information related to each of the images. The accompanying information to be displayed can be determined freely. In this embodiment, the additional information, the patient information, the medical examination information, the series information, and the image unit information which comprise the accompanying information are shown in the display areas 21~25. The additional information is information not relevant to the information in other display areas, such as the name of a radiologist having photographed the image and the photographing room in which the image was photographed. The patient information refers to information related to a patient as a subject of the image, such as the name, date of birth, and gender of the patient. The medical examination information refers to information related to a medical examination. The medical examination information includes a medical examination number indicating a type of medical examination such as chest examination or abdomen examination. The series information refers to information regarding a series of images, and includes a series number indicating which series the image belongs to, for example. The series of images refers to a group of images photographed at one time. In this embodiment, one series comprises one or more images and one medical examination comprises one or more series. The image unit information is information related to each image unit, that is, information based on each image. The image unit information includes the name of a photographing menu, and a standardization condition of the image, for example.

When the images and the accompanying information thereof are input from the external system 50 to the control unit 4, the images and the information are stored in the storing means 2 by being linked to each other, that is, by being related to each other. At the same time, image list display control means 30 of the control unit 4 carries out image reduction processing for generating reduced images by reducing the number of image signals through signal thinning processing or interpolation processing on the images having been input. In this manner, reduced monitor images and thumbnail images having a larger reduction ratio than the monitor images are generated and sequentially input to the monitor display area 11 and the thumbnail image display area 12 to be sequentially displayed therein. The accompanying information is sequentially displayed in the accompanying information display area 20 in the form of the list.

More specifically, when a first image and a first accompanying information item which is the accompanying information to be linked with the first image are input, the first image and the first accompanying information item are stored in the storing means 2 while being linked to each other. The image list display control means 30 generates a reduced monitor image to be displayed in the monitor display area 11 by reducing the first image having been input, and displays the first accompanying information item in a lowermost line 20-1 in the accompanying information display area 20.

When a second image and a second accompanying information item are input, the second image and the second accompanying information item are stored in the storing means 2 by being linked to each other, and the image list display control means 30 generates a reduced monitor image to be displayed in the monitor display area 11 by reducing the second image having been input. At the same time, the image list display control means 30 generates a thumbnail image to be displayed in a first display frame 13-1 in the thumbnail image display area 12 by reducing the first image while displaying the second accompanying information item in the lowermost line 20-1 in the accompanying information display area 20. The image list display control means 30 shifts the first accompanying information item to a line 20-2 immediately above the lowermost line.

Thereafter, each time a new image is input, the same procedure is repeated. The newly input image and the accompanying information item thereof are stored in the storing means 2. At the same time, a reduced monitor image of the newly input image is displayed in the monitor display area 11 while the thumbnail images of the preceding images are displayed by shifting the display frames 13 one by one in the direction of an arrow. Meanwhile, the newly input accompanying information item is displayed in the lowermost line 20-1 of the accompanying information display area 20 while the preceding accompanying information items are displayed by shifting the lines one by one.

After the thumbnail image of the first image has been moved to a 24th frame 13-24 and the accompanying information item thereof has been shifted to an uppermost line 20-25 in the accompanying information display area 20, the thumbnail image in the last frame 13-24 is eliminated from the thumbnail image display area 12 and disappears from the screen 3 when a new image and an accompanying information item thereof are input. Meanwhile, the accompanying information item displayed in the uppermost line 20-25 is also eliminated from the accompanying information display area 20 and disappears from the screen 3.

Each of the accompanying information items of the respective images are displayed in one line, and the additional information, the patient information, the medical examination information, the series information, and the image unit information are displayed in the additional information display area 21, the patient information display area 22, the medical examination information display area 23, the series information display area 24, and the image unit information display area 25, respectively.

A mouse 5*a* or a keyboard 5*b* comprising the instruction input means 5 has a function of inputting a scrolling instruction. When the scrolling instruction is input from the instruction input means 5 to the control unit 4, the image list display control means 30 redisplays in the accompanying information display area 20 the accompanying information items having been eliminated from the accompanying information display area 20, by scrolling the accompanying information display area 20.

Image selection in the above apparatus will be explained next.

The accompanying information of the images is equivalent to image properties in the present invention. In other words, the name of each patient, each examination number, each series number, and the like are the image properties. In this case, the patient, the examination, and the series are used as property items. In this embodiment, the property items comprise items of the patient, the examination, and the series, and these items have a hierarchical structure. The patient item is set to the highest level followed by the examination item in a subsequent level. The series item is set to the lowest level.

The control unit 4 comprises collective image selection means 31. When a desired one of the images and a desired one of the property items are specified by the instruction input means 5, the collective image selection means 31 carries out collective image selection based on the image and the property item having been specified by the instruction input means 5.

In other words, the instruction input means 5 serves as image specifying means and property item specifying means. The instruction input means 5 specifies one of the images in the image list on the screen 3. For example, by clicking the mouse 5*a* on a left button thereof after moving a pointer to the line in which the accompanying information item of the desired image is being displayed, the image in the line (the image related to the accompanying information item in the line) is specified.

Figure 3:
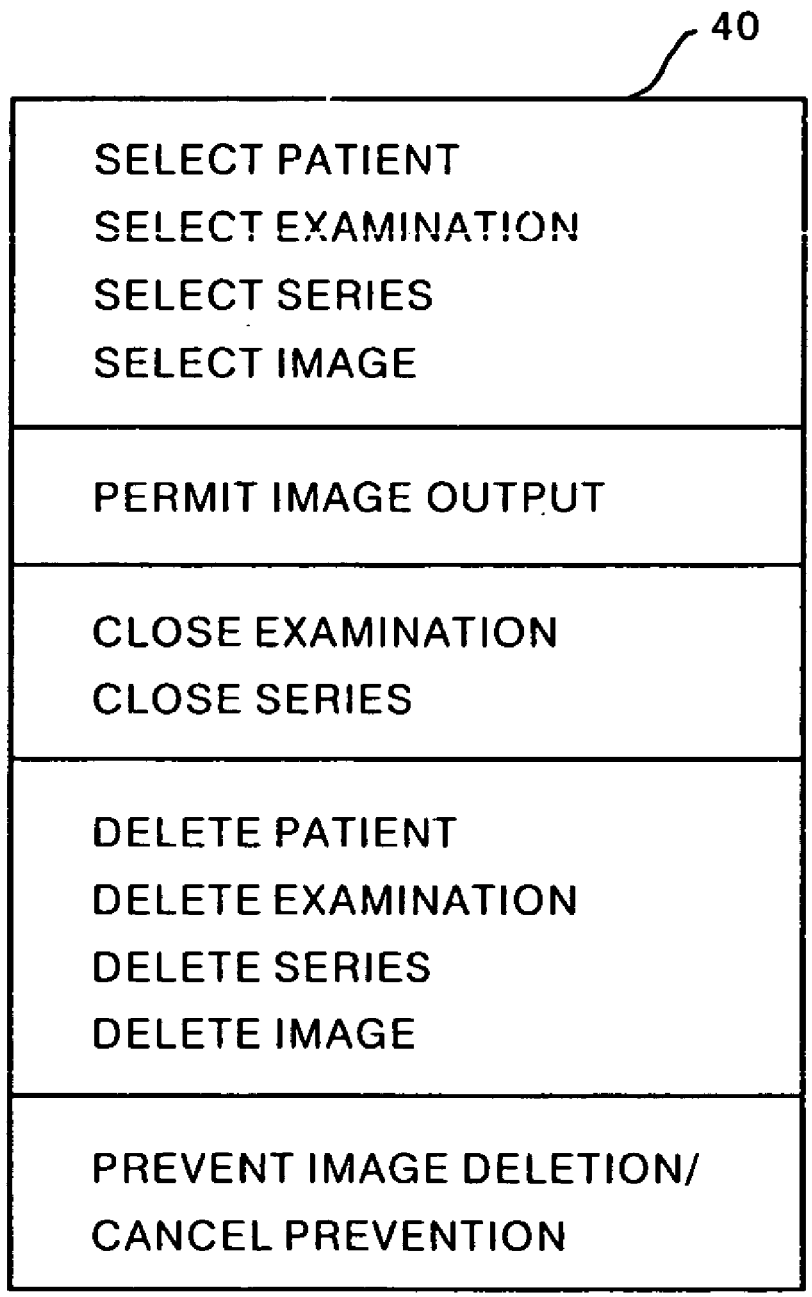
FIG. 3 is an example of a property item menu.

A property item menu is then opened by clicking the mouse 5*a* on a right button thereof, and the desired property item is selected from the menu. For example, a property item menu 40 shown in FIG. 3 is displayed on the screen 3 by right-click of the mouse 5*a*, and the pointer is moved to a line of the desired property item. By left-click of the mouse 5*a* on the line, the property item in the line is specified.

After the image and the property item have been specified in the above manner, the collective image selection means 31 recognizes the property (accompanying information) of the specified property item of the image having been specified, and searches for all images having the same property from the storing means 2. In this manner, the images having the same property are collectively selected by the collective image selection means 31. In this embodiment, the image list display control means 30 reverses brightness of the lines in which the accompanying information items of the images having been selected are displayed when the images are selected.

This selection will be explained below in detail.

"Select patient" in an uppermost line of the menu 40 refers to the property item "patient". Therefore, when this line is specified, all images for the same patient as the image having been specified are searched for and selected.

"Select examination" in a second line from the top of the menu 40 refers to the property item "examination". In this embodiment, the property items have the hierarchical structure with the patient being in the highest level followed by the examination and the series in this order. The collective image selection means 31 collectively selects all images having the same properties as in the property items in the level of the property item having been specified and in the higher levels, in the case where the property item having been specified is not in the highest level. Therefore, when "select examination" is specified, all images having the same properties as in the property item "examination" and as in the property item "patient" which is in the level higher than the level of the property item "examination" are searched for and selected. For example, when the image having been specified is an image of a patient A and the examination number in the specified property item is 1, all images of the patient A having the examination number 1 are searched for and selected.

"Select series" in a third line in the menu 40 refers to the property item "series". When this line is specified, images having the same properties as in the property item "series" and in the property items "examination" and "patient" in the higher levels are selected, since the property items have the hierarchical structure. For example, if the image having been specified is an image of the patient A and if the examination number and the series number are 1 and 1 respectively, all images for the patient A having the examination number 1 and the series number 1 are searched for and selected.

"Select image" in a fourth line in the menu 40 refers to no property item but refers to an image selection instruction. When this line is specified, the collective image selection means 31 simply selects the image specified by the instruction input means 5 (image specifying means).

"Permit image output" in a fifth line in the menu 40 does not refer to any property item but refers to an image output/display instruction. In other words, when this line is specified, the instruction input means 5 serves as output/display instruction means and specifying this line indicates inputting the image output/display instruction. In this case, output/display control means 32 displays on the screen 3 the images having been selected according to specification of any of the first to fourth lines, by receiving the output/display instruction. In this embodiment, the images to be displayed are shown in windows W of a predetermined size at predetermined positions on the screen 3, overlapping one another with a slight shift. A viewer can observe the images by clicking on the images one by one. However, the method of display is not necessarily limited to this example, and other methods, such as displaying all the images in the same size in rows on the screen 3, may be adopted.

"Close examination" in a sixth line in the menu 40 specifies the property item "examination" and refers to a closing instruction. In other words, the instruction input means 5 has a function of instructing closing. As in the case of selecting "select examination", when the "close examination" is specified, the collective image selection means 31 searches for and selects all the images having the same properties as the image whose properties have been specified in the property item "examination" and in the higher-level property item "patient". At the same time, closing means 33 in the control unit 4 writes information "examination closed" to the images having been selected. The information "examination closed" is written to prevent various problems which would occur due to a suspended examination, such as in the case where 10 images are to be photographed in a medical examination but photographing is suspended for some reason after 5 images have been photographed. Therefore, "examination closed" is written to indicate that the examination has been finished with only the 5 images.

"Close series" in a seventh line in the menu 40 specifies the property item "series" and refers to a closing instruction. As in the case of selecting "select series", when "close series" is specified, the collective image selection means 31 searches for and selects all the images having the same properties as the image whose properties have been specified, in the property item "series", and in the property items "examination" and "patient" in the higher levels. At the same time, the closing means 33 in the control unit 4 writes information "series closed" to all the images having been selected. As in the case of the information "examination closed", the information "series closed" is written to indicate the end of the series in the case where photographing is suspended for some reason before a predetermined number of images have been photographed.

"Delete patient", "delete examination", and "delete series" in the eighth to tenth lines in the menu 40 respectively specify the property items "patient", "examination", and "series", and refer to deletion instructions. In other words, the input instruction means 5 serves as deletion instruction means. When each of these lines is specified, the collective image selection means 31 selects the images as in the case of specifying "select patient", "select examination" or "select series", and deletion means 34 in the control unit 4 deletes from the storing means 2 the images having been selected.

"Delete image" in an eleventh line in the menu 40 does not refer to any property item but refers to an image deletion instruction. When this line is specified, the deletion means 34 simply deletes the image having been specified by the instruction input means 5 (image specifying means).

"Prevent image deletion/cancel prevention" in the lowermost line in the menu 40 refers to an instruction of image deletion prevention or cancellation thereof. In other words, the instruction input means 5 has functions of instructing prevention of image deletion and cancellation thereof. When the eleventh line is specified, deletion prevention/cancellation means 35 in the control unit 4 carries out deletion prevention and deletion prevention cancellation on the images having been selected according to the specification of the first to fourth lines in the menu 40. When the storing means 2 becomes full of the images and the accompanying information thereof, an oldest image and the accompanying information item thereof are automatically deleted from the storing means 2 when a new image and an accompanying information item thereof are input. "Prevent image deletion" is to prohibit this automatic image deletion and "cancel prevention" is to cancel the deletion prevention. When this line is specified for an image for which deletion is not currently prevented, the image is becomes protected against being deleted. On the other hand, when this line is selected for an image for deletion is currently prevented, the deletion prevention is cancelled.

The first to fourth lines in the menu 40 simply select the images. However, if the images are selected according to these lines and if the images having been selected are shown as the selected images by being displayed as reversed images or by using any other methods, convenience is improved in the case where all the images regarding a patient need to be confirmed or the quantity of images having been photographed in a medical examination needs to be checked, for example. Furthermore, various kinds of processing including output/display and deletion can be carried out on such images selected in the above manner.

In this embodiment, the list of the accompanying information (properties) is used as the image list. However, any list of information enabling specification of each image can be used as the image list in the present invention, and the information is not limited to the accompanying information described above.

Furthermore, the present invention is applicable not only to transmission of the images recorded on the stimulable phosphor sheets but also transmission of other kinds of images.

In addition, all of the contents of Japanese Patent Application No. 11(1999)-312144 are incorporated into this specification by reference.

What is claimed is:

1. An image selecting apparatus comprising:
   storing means for storing a plurality of images;
   a display screen for displaying a list of the images stored in the storing means;
   image specifying means for specifying a desired one of the images from the image list displayed on the screen;
   property item specifying means for specifying a desired one of image property items; and
   collective image selection means for collectively selecting, in the case where the desired one of the images has been specified by the image specifying means and the desired one of image property items has been specified, all stored images having the same property as in the specified image property item of the specified image,
   wherein the image property items have a hierarchical structure and the collective image selection means collectively selects, in the case where the specified image property item is in a hierarchical level other than a highest level, all images having the same properties as in the property items in the hierarchical level of the specified property item and in higher levels and
   the hierarchical structure of the image property items includes a plurality of image property items having a plurality of hierarchical levels which are higher than that of "Image" and lower than that of "Patient"; and
   the property item specifying means specifies a desired one of image property items at each level.

2. An image selecting apparatus as defined in claim 1, wherein the collective image selection means collectively selects the images from all the images stored in the storing means.

3. An image selecting apparatus as defined in claim 1, further comprising:
   output/display instruction means for inputting an output/display instruction for outputting or displaying the images having been collectively selected; and
   output/display control means for outputting or displaying the images having been collectively selected, based on the output/display instruction.

4. An image selecting apparatus as defined in claim 1, further comprising:
   deletion instruction means for inputting a deletion instruction to delete, from the storing means, the images having been collectively selected; and
   deletion means for deleting the images from the storing means by receiving the deletion instruction.

5. An image selecting apparatus as defined in claim 1, wherein the property item specifying means specifies a desired one of properties of the specified image.

6. An image selecting apparatus as defined in claim 1, wherein the property item specifying means specifies a desired one of properties of the specified image.

7. An image selecting apparatus as defined in claim 1, wherein the image property items comprises at least one of patient information, type of medical examination, and series information identifying a group of images captured in a medical examination.

8. An image selecting apparatus as defined in claim 7, wherein the image property items comprises patient information, type of medical examination, and series information.

9. An image selecting apparatus as defined in claim 1, wherein the image property items comprises at least one of patient information, type of medical examination, and series information identifying a group of images captured in a medical examination.

10. An image selecting apparatus as defined in claim 9, wherein the image property items comprises patient information, type of medical examination, and series information.

11. An image selecting apparatus as defined in claim 1, wherein the collective image selection means searches the storing means for the all stored images having the same property, to collectively select the all stored images having the same property.

12. An image selecting apparatus as defined in claim 1, wherein the collective image selection means recognizes the specified image property item of the specified image and searches the storing means for the all stored images having the same property, to collectively select the all stored images having the same property.

13. An image selecting apparatus as defined in claim 1, wherein after the desired one of the images is specified, the property item specifying means displays a menu listing the image property items in response to the image being specified, and each of image property items having a property therein.

14. An image selecting apparatus as defined in claim 1, wherein the image property items of an image are generic to other images.

15. An image selecting apparatus as defined in claim 1, wherein multiple stored images are collectively selected by the collective image selection means.

16. An image selecting apparatus as defined in claim 1, wherein all the images having the same property as in the specified image property item of the specified image are stored in the storing means.

17. An image selecting apparatus as defined in claim 1, wherein the "Image" is the desired one of the images and the "Patient" is a means for identifying a patient.

18. An image selecting apparatus as defined in claim 1, wherein the image property items comprises;
   a means for identifying a patient of the desired one of the images;
   the desired one of the images; and
   a plurality of image property items having a plurality of hierarchical levels which are higher than a hierarchical level of the desired one of the images and lower than a hierarchical level of the means for identifying the patient.

19. A method of processing images comprising:
   storing a plurality of images;
   displaying a list of the images stored;
   specifying a desired one of the images from the image list displayed;
   specifying a desired one of image property items of the specified image; and
   collectively selecting all stored images of the plurality of images having the same property as in the specified image property item of the specified image,
   wherein the image property items have a hierarchical structure and wherein the step of collectively selecting all images selects, in the case where the specified image property item is in a hierarchical level other than a highest level, all images having the same properties as in the property items in the hierarchical level of the specified property item and in higher levels and
   the hierarchical structure of the image property items includes a plurality of image property items having a plurality of hierarchical levels which are higher than that of "Image" and lower than that of "Patient", and
   the property item specifying means specifies a desired one of image property items at each level.

20. An image processing method as defined in claim 19, wherein the step of collectively selecting all images selects the images from all the stored images.

21. An image processing method as defined in claim 19, further comprising:
   inputting an output/display instruction for outputting or displaying the collectively selected images; and
   outputting or displaying the collectively selected images, based on the inputted output/display instruction.

22. An image processing method as defined in claim 19, further comprising:
   inputting a deletion instruction to delete, from among the stored images, the collectively selected images; and
   deleting the collectively selected images from among the stored images by receiving the deletion instruction.

* * * * *